(12) United States Patent
Morris et al.

(10) Patent No.: US 9,839,765 B2
(45) Date of Patent: Dec. 12, 2017

(54) TRANSFEMORAL MITRAL VALVE REPAIR DELIVERY DEVICE

(71) Applicant: St. Jude Medical, Cardiology Division, Inc., St. Paul, MN (US)

(72) Inventors: Benjamin E. Morris, Jeffersonville, IN (US); Wayne Johnson, Jeffersonville, IN (US); Mark Griffin, Louisville, KY (US); Cory Celestino, Floyd Knobs, IN (US); Jeffrey Clarke, Jeffersonville, IN (US); Indi Gunasekara, Louisville, KY (US); Gregory R. Furnish, Louisville, KY (US); Theodore Paul Dale, Corcoran, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 382 days.

(21) Appl. No.: 14/532,149

(22) Filed: Nov. 4, 2014

(65) Prior Publication Data
US 2015/0134053 A1 May 14, 2015

Related U.S. Application Data

(60) Provisional application No. 61/902,964, filed on Nov. 12, 2013, provisional application No. 61/903,095, filed on Nov. 12, 2013.

(51) Int. Cl.
*A61F 2/24* (2006.01)
*A61M 25/01* (2006.01)
(Continued)

(52) U.S. Cl.
CPC ....... *A61M 25/0113* (2013.01); *A61F 2/2427* (2013.01); *A61M 25/0013* (2013.01);
(Continued)

(58) Field of Classification Search
CPC ...... A61F 2/2427; A61F 2/243; A61F 2/2433; A61F 2/2436; A61F 2/2439;
(Continued)

(56) References Cited

U.S. PATENT DOCUMENTS

2003/0009195 A1* 1/2003 Field .................. A61B 17/0469
606/219
2004/0049207 A1* 3/2004 Goldfarb ................ A61B 50/30
606/139
(Continued)

FOREIGN PATENT DOCUMENTS

CA    WO02/34167    * 10/2000    ............... A61F 2/24
WO    2013116617 A1    8/2013

OTHER PUBLICATIONS

Extended European Search Report for Application No. 14192256 dated Feb. 9, 2015.

*Primary Examiner* — Katrina Stransky
*Assistant Examiner* — Marie C Black
(74) *Attorney, Agent, or Firm* — Lerner, David, Littenberg, Krumholz & Mentlik, LLP

(57) ABSTRACT

A device for repair of a heart valve leaflet includes an elongated catheter assembly having a proximal end and a distal end, and a tip at the distal end of the catheter assembly. A capture mechanism having a first free end and a second free end is rotatably coupled to a distal end of the tip. A plication mechanism has an open configuration and a closed configuration, and extends between the first free end and the second free end of the capture mechanism when in the open configuration. The device may also include a clip housing at a proximal end of the tip configured to hold a clip therein.

19 Claims, 12 Drawing Sheets

(51) Int. Cl.
*A61M 25/00* (2006.01)
*A61M 25/06* (2006.01)
*A61B 17/00* (2006.01)

(52) U.S. Cl.
CPC .... *A61M 25/0054* (2013.01); *A61M 25/0133* (2013.01); *A61M 25/0136* (2013.01); *A61M 25/0138* (2013.01); *A61M 25/0147* (2013.01); *A61M 25/0662* (2013.01); *A61B 2017/00309* (2013.01); *A61B 2017/00323* (2013.01)

(58) Field of Classification Search
CPC ............. A61F 2/2469; A61M 25/0014; A61M 25/0054; A61M 25/0013; A61M 25/0136; A61M 25/0138; A61M 25/0147; A61M 25/0662
USPC ........................................................ 623/2.11
See application file for complete search history.

(56) References Cited

U.S. PATENT DOCUMENTS

| | | | |
|---|---|---|---|
| 2005/0240202 A1 | 10/2005 | Shennib et al. | |
| 2005/0267529 A1 | 12/2005 | Crockett et al. | |
| 2008/0294175 A1* | 11/2008 | Bardsley | A61B 17/12009 606/113 |
| 2010/0331971 A1* | 12/2010 | Keranen | A61F 2/2445 623/2.11 |
| 2012/0259356 A1* | 10/2012 | Khairkhahan | A61B 17/0057 606/194 |
| 2012/0330407 A1* | 12/2012 | Dale | A61B 17/122 623/2.11 |

* cited by examiner

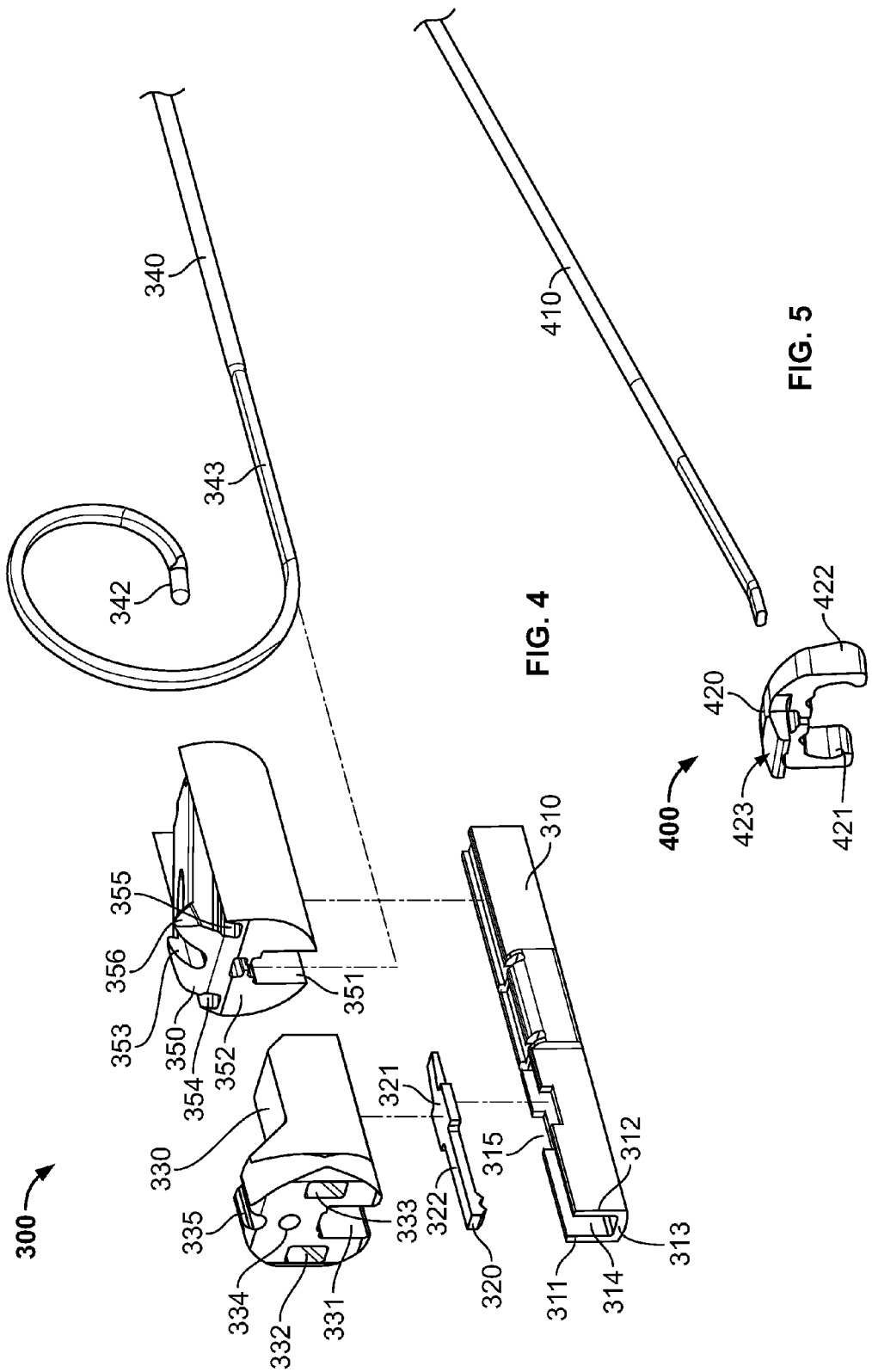

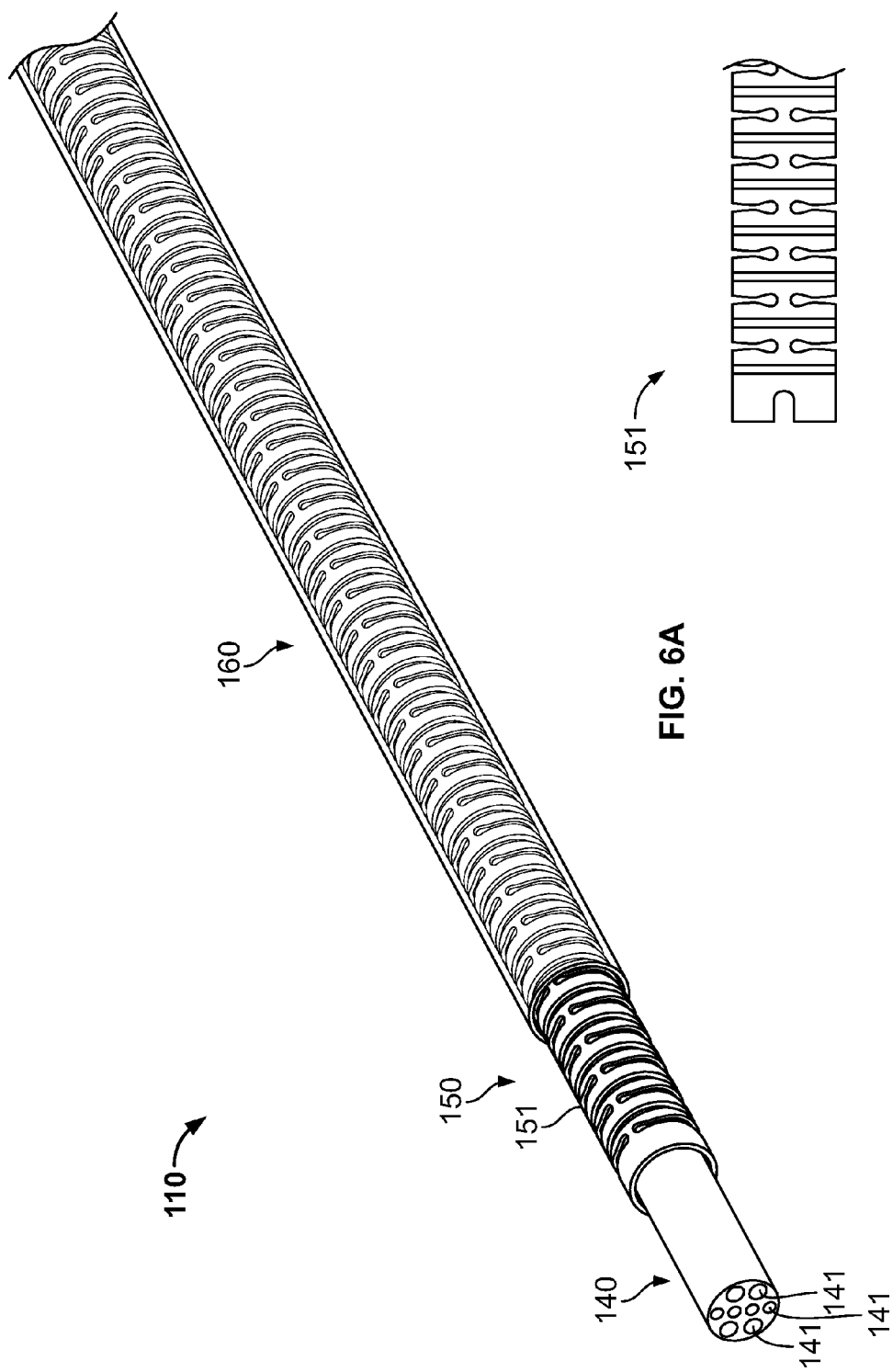
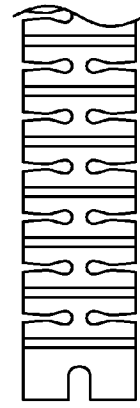
FIG. 6A
FIG. 6B

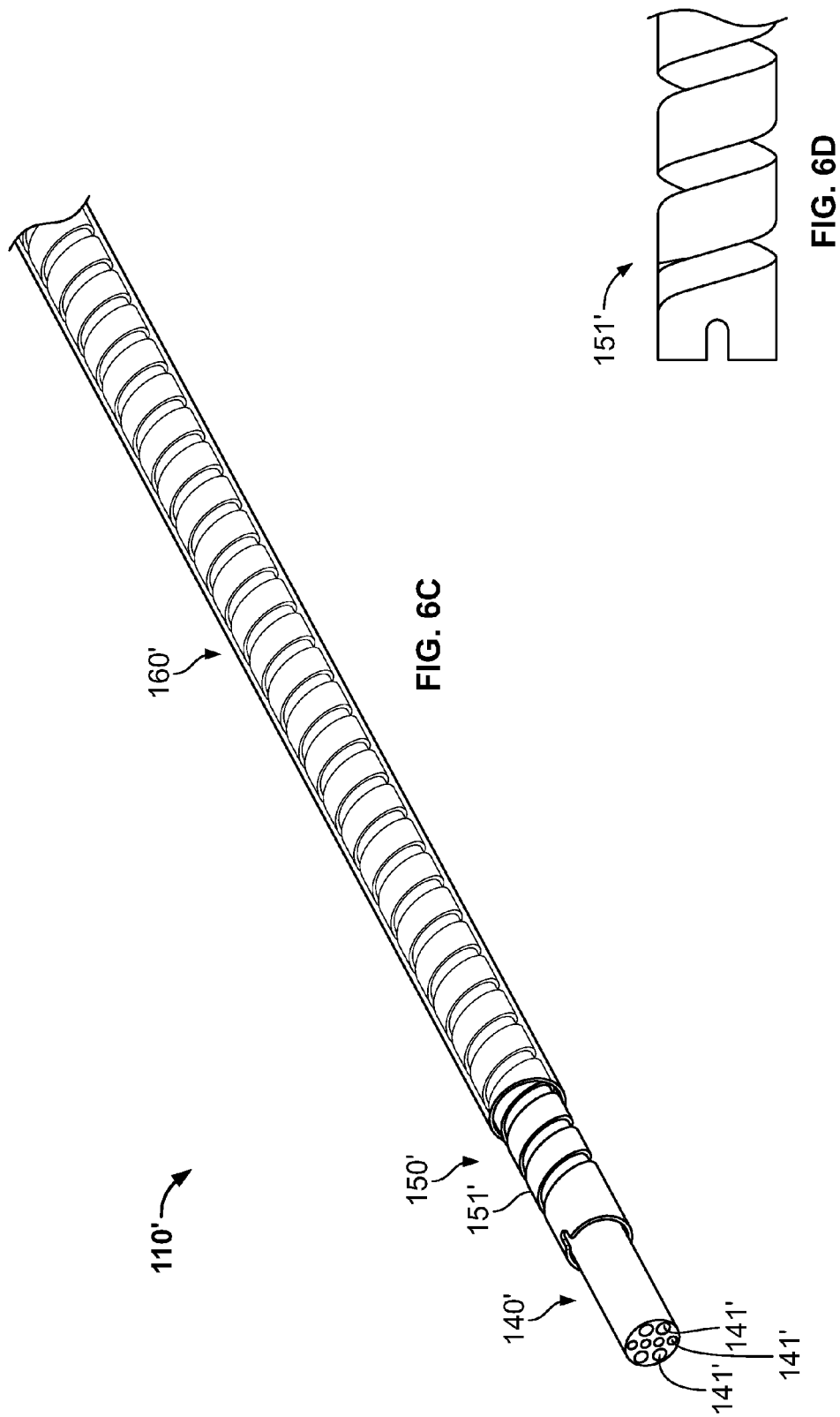

TRANSFEMORAL MITRAL VALVE REPAIR DELIVERY DEVICE

CROSS-REFERENCE TO RELATED APPLICATIONS

The present application claims the benefit of the filing date of U.S. Provisional Patent Application No. 61/902,964 filed Nov. 12, 2013, and U.S. Provisional Patent Application No. 61/903,095 filed Nov. 12, 2013, the disclosures of which are both hereby incorporated by reference herein.

BACKGROUND

The present disclosure is related to tissue repair, and more particularly to devices, systems, and methods for repair of a heart valve leaflet.

Properly functioning heart valves can maintain unidirectional blood flow in the circulatory system by opening and closing, depending on the difference in pressure from one side of the valve to the other. The two atrioventricular valves (mitral and tricuspid valves) are multicuspid valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be ruptured. As a result, the valve does not close normally and the unsupported valve leaflet may bulge back, or "prolapse," into the left atrium like a parachute. Thus, as the ventricle contracts, the abnormal leaflet may be propelled backwards, beyond its normal closure line and into the left atrium, thereby allowing blood to return to the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

BRIEF SUMMARY

In one embodiment, a device for repair of a heart valve leaflet includes an elongated catheter assembly having a proximal end and a distal end, and a tip at the distal end of the catheter assembly. A capture mechanism having a first free end and a second free end is rotatably coupled to a distal end of the tip. A plication mechanism has an open configuration and a closed configuration, and extends between the first free end and the second free end of the capture mechanism when in the open configuration. The device may also include a clip housing at a proximal end of the tip configured to hold a clip therein.

BRIEF DESCRIPTION OF THE DRAWINGS

FIG. 4 is an exploded view of a ramp subassembly of the repair device of FIG. 2.

FIG. 5 is an exploded view of a carriage assembly of the repair device of FIG. 2.

FIG. 6A is a perspective cutaway view of a catheter subassembly of the repair device of FIG. 2.

FIG. 6B is a plan view of a portion of a patterned tube of the catheter subassembly of FIG. 6A.

FIG. 6C is a perspective cutaway view of an alternate embodiment of a catheter subassembly.

FIG. 6D is a plan view of a portion of a patterned tube of the catheter subassembly of FIG. 6C.

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. Aspects of the disclosure will be described in connection with the repair of a mitral valve leaflet, but it may also be useful in the repair of other types of cardiac valves or in the gathering and securing of other types of loose body tissue.

Figure 1:
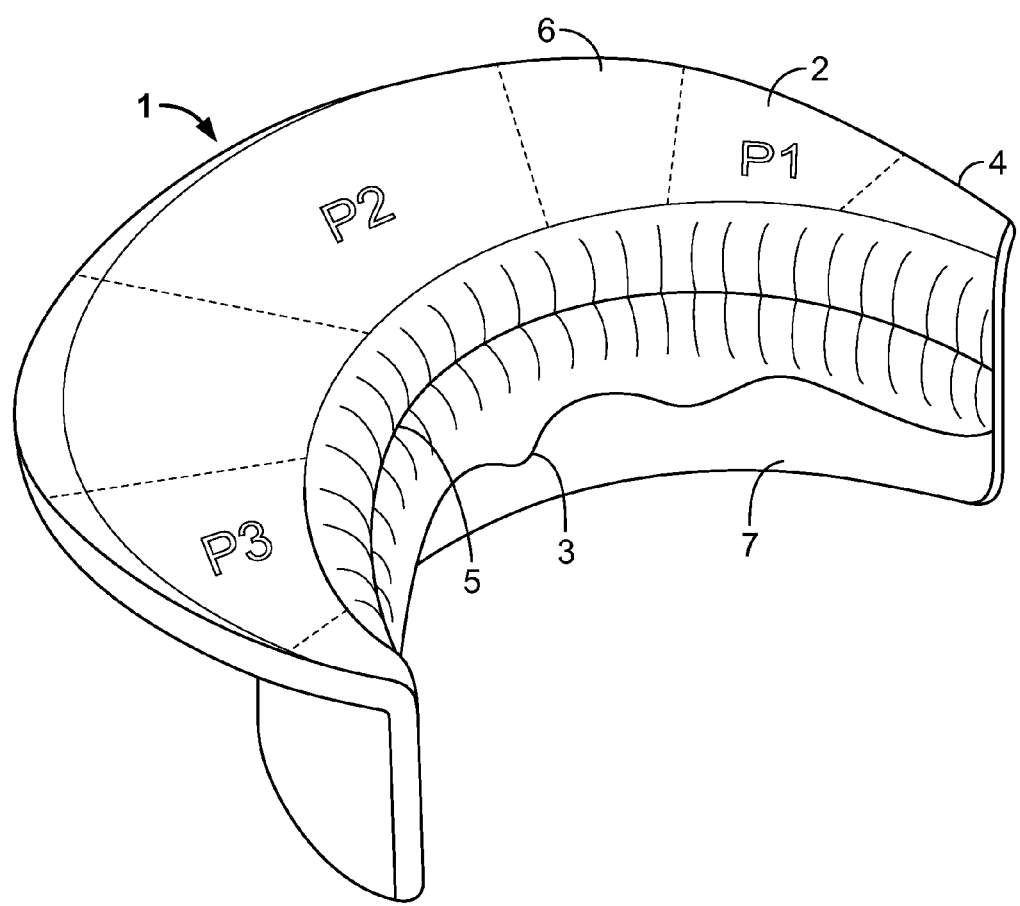
FIG. 1 is a diagrammatic perspective view of the posterior leaflet of a mitral valve.

As shown in FIG. 1, an exemplary mitral valve 1 includes a posterior leaflet 2 and a portion of an anterior leaflet 3. The leaflets 2 and 3 extend from an annulus 4 to a coaptation line 5 where the leaflets meet. The posterior leaflet 2 has an upper portion 6 that is generally perpendicular to the direction of blood flow through the valve 1 and extends between the annulus 4 and the coaptation line 5. Additionally, the posterior leaflet 2 has a lower portion 7 that is generally parallel to the direction of blood flow through the valve 1 and extends below the coaptation line 5. The posterior leaflet 2 has three scalloped portions P1, P2, and P3, any of which may include a portion that is billowed, loose, or floppy, and therefore can be the cause of a prolapse condition of the valve. The devices, systems, and methods described herein may be adapted to repair such a billowed, loose, or floppy portion of the posterior leaflet 2 or the anterior leaflet 3.

Figure 2:
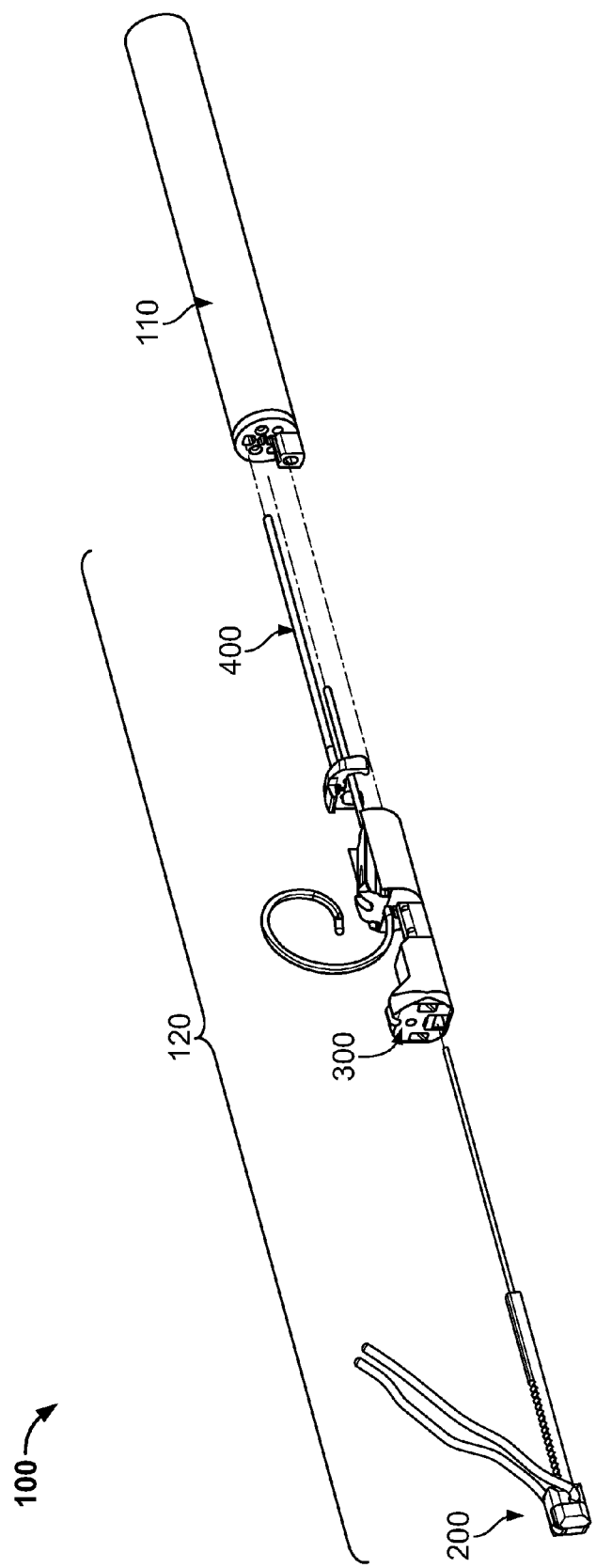
FIG. 2 is an exploded view of a mitral valve repair device.

Referring to FIG. 2, a device 100 for repair of heart valve leaflet tissue is shown in exploded view. The device 100 may include an elongated body or catheter assembly 110 adapted to be inserted into the left atrium or left ventricle of a human heart so that a distal portion or tip 120 of the device 100 may reach the patient's mitral valve 1 for repair thereof. Once near the mitral valve 1, different components of the device 100 may be actuated to repair the mitral valve 1, as is discussed more completely below following the description of the components of the device 100. It should be noted that the device 100 may be employed near the posterior leaflet 2, the anterior leaflet 3, or any other suitable tissue within the heart or similar tissue.

Still referring to FIG. 2, the device 100 generally includes a number of assemblies or subassemblies, including the catheter assembly 110, a capture subassembly 200, a ramp subassembly 300, and a carriage assembly 400. The catheter assembly 110 may include a proximal end 130 attached to a handle 500 (shown in FIG. 7).

Figure 3A:
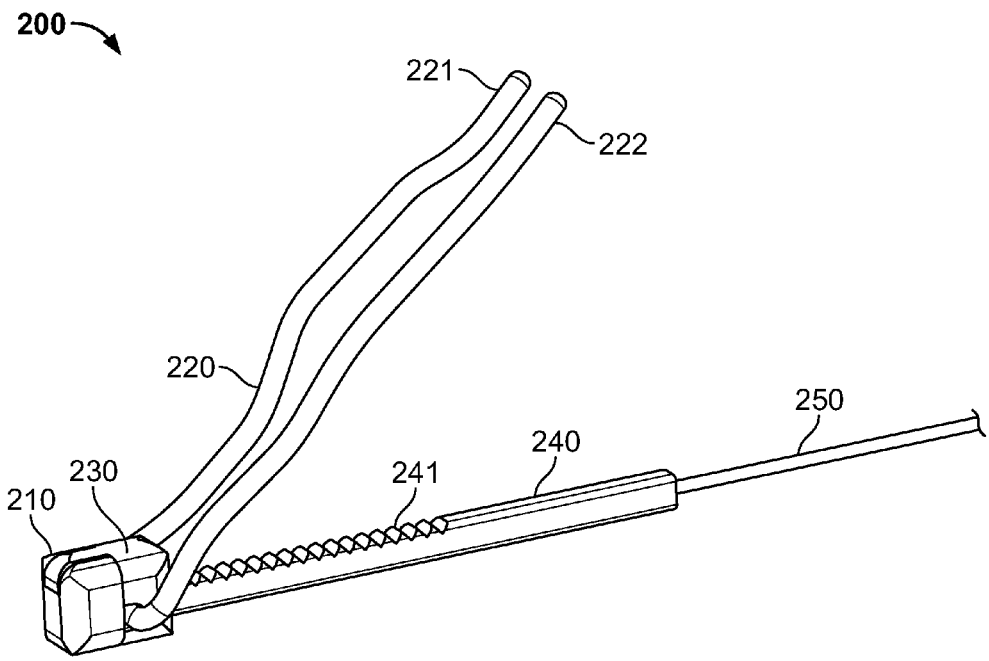
FIGS. 3A-B are perspective and exploded views of a capture subassembly of the repair device of FIG. 2.
Figure 3B:
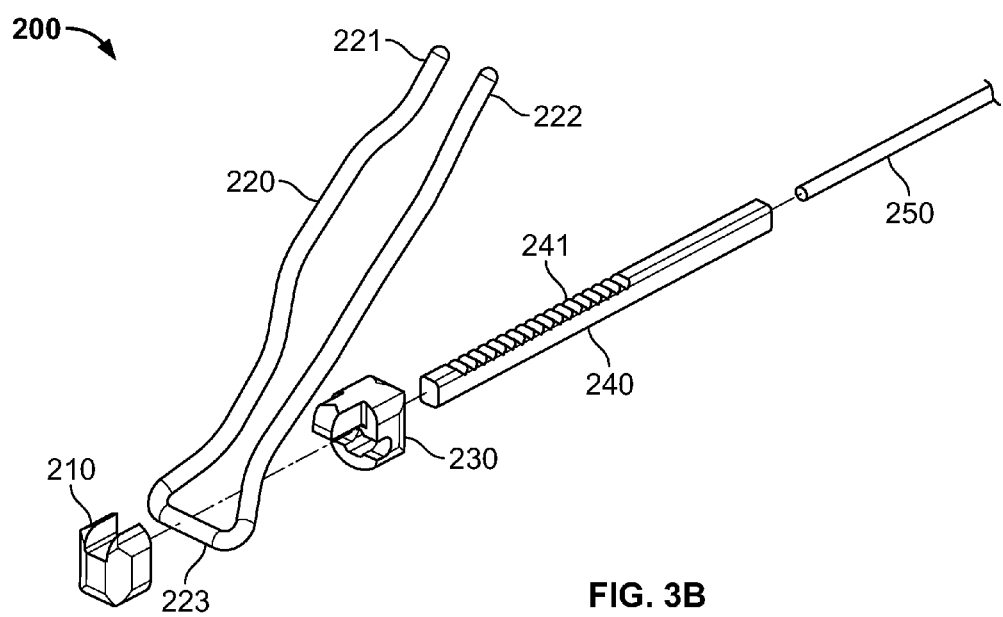

The capture subassembly 200, shown in FIGS. 3A-B, includes a pivot tip lock 210, a capture mechanism such as capture wire 220, a pivot tip 230, a reinforcement tube 240, and a pivot tip wire 250. Generally, the capture subassembly 200 functions to make contact with and grasp tissue in the mitral valve 1. The capture wire 220 may be formed of a single wire including first free end 221 and a second free end 222 by a central portion 223. The pivot tip 230 and pivot tip lock 210 may be joined over the central portion 223 of the capture wire 220, the pivot tip 230 and the pivot tip lock 210 forming an aperture (not labeled) in which the central portion 223 of the capture wire 220 may rotate. The rotation of the central portion 223 of the capture wire 220 also causes the free ends 221, 222 of the capture wire 220 to rotate about the central portion 223. This rotation provides, in part, the ability of the capture wire to grasp tissue in the mitral valve 1.

To form the capture wire 220, a length of stainless steel wire may be inserted in the aperture defined by the pivot tip 230 and pivot tip lock 210 and then bent, for example using wire holders and pliers, to the desired shape. Other processes may also be suitable to form the desired geometry of capture wire 220, such as computer numerical control ("CNC") wire forming, stamping with a die, four slide wire forming, etc. The shape may be generally "U"-shaped or "V"-shaped, but other shapes may be suitable. Similarly, it should be understood that the capture wire 220 may be formed of other suitable biocompatible materials other than stainless steel. In one embodiment, end portions of the free ends 221, 222 of the capture wire 220 may be bent or angled toward the catheter assembly 110. The end portions of the free ends 221, 222 may be bent with a shallow angle, for example less than 45 degrees, less than 30 degrees, or less than 15 degrees with respect to the rest of the free ends 221, 222. This shallow angle may, for example, pinch the tissue during use, as described in greater detail below, applying a focused force compressing the tissue better. This, in turn, may provide a more optimal condition for applying a clip to the plicated tissue.

Still referring to FIGS. 3A-B, the reinforcing tube 240 may be coupled to the proximal end of the pivot tip 230. Some or all of a surface of the reinforcing tube 240 may include texturing 241, such as ribs, grooves, or teeth (best illustrated in FIG. 9A). The texturing 241 may correspond with a structure on the ramp subassembly 300 (described below in relation to FIG. 4), such as a rib, groove, or tooth, to allow for incremental or discrete movement and/or locking of the reinforcing tube 240. The pivot tip wire 250 may extend through a lumen 141 (FIG. 6A) in the catheter assembly 110 and extend to the handle 500.

The ramp subassembly 300 is shown in FIG. 4. Generally, the ramp subassembly 300 includes an actuator rail 310, an actuator lock 320, an actuator 330, a plication mechanism such as a plication wire 340, and a clip housing 350. The actuator rail 310 may include first and second generally parallel walls 311, 312 connected by a third wall 313. The three walls 311-313 may define a slot 314 in the rail 310 and form a general "U"-shaped cross section. The reinforcing tube 240 and pivot tip wire 250 of the capture subassembly 200 may extend through the slot 314 of the actuator rail 310.

The actuator lock 320 may include a plate 321 that couples with a corresponding recess 315 defined by the first and second walls 311, 312. The actuator lock 320 may also be rigidly fixed to the actuator 330. The actuator lock may also include a locking element 322, such as a tooth, rib, or finger that extends distally from the plate 321. Preferably, the locking element 322 is not coupled to either wall 311, 312 of the actuator rail 310. With this configuration, as successive ribs or teeth of the textured surface 241 of the reinforcing tube 240 pass across the locking element 322, the locking element 322 will successively slide over the ribs or teeth of the textured surface 241. When the locking wire 710 (illustrated in FIG. 9B) is advanced by the locking wire button 570 (described in more detail below with reference to FIG. 7), it fills the vacant area between the locking element 322 and the top of the recess 331. This prevents the intermeshed ribs or teeth 241 of the reinforcing tube 240 and the locking element 322 from sliding relative to one another, thus preventing unwanted movement of the capture wire 220. The frictional engagement between the textured surface 241 and the locking element 322 may provide enough force to resist unintended movement of the reinforcing tube 241 with respect to the actuator 330, actuator lock 320, and actuator rail 310.

The actuator 330 may have a generally rectangular or tubular proximal end that increases in size toward the distal end, with a recess 331 extending from the proximal end to the distal end. The recess 331 may generally correspond to the shape of the actuator rail 310 such that the recess 331 fits over the side walls 311, 312 of the actuator rail 310. A distal face of the actuator 330 may include two through-holes 332, 333. Each through-hole 332, 333 may be ramped downward from the proximal end toward the distal end, and be shaped to receive respective free ends 221, 222 of the capture wire 220. Movement of the actuator 330 (and thus actuator through-holes 332, 333) with respect to the free ends 221, 222 of the capture wire 220 causes the capture wire 220 to rotate open or closed. This function is explained in greater detail below with respect to FIGS. 9A-D.

Figure 9A:
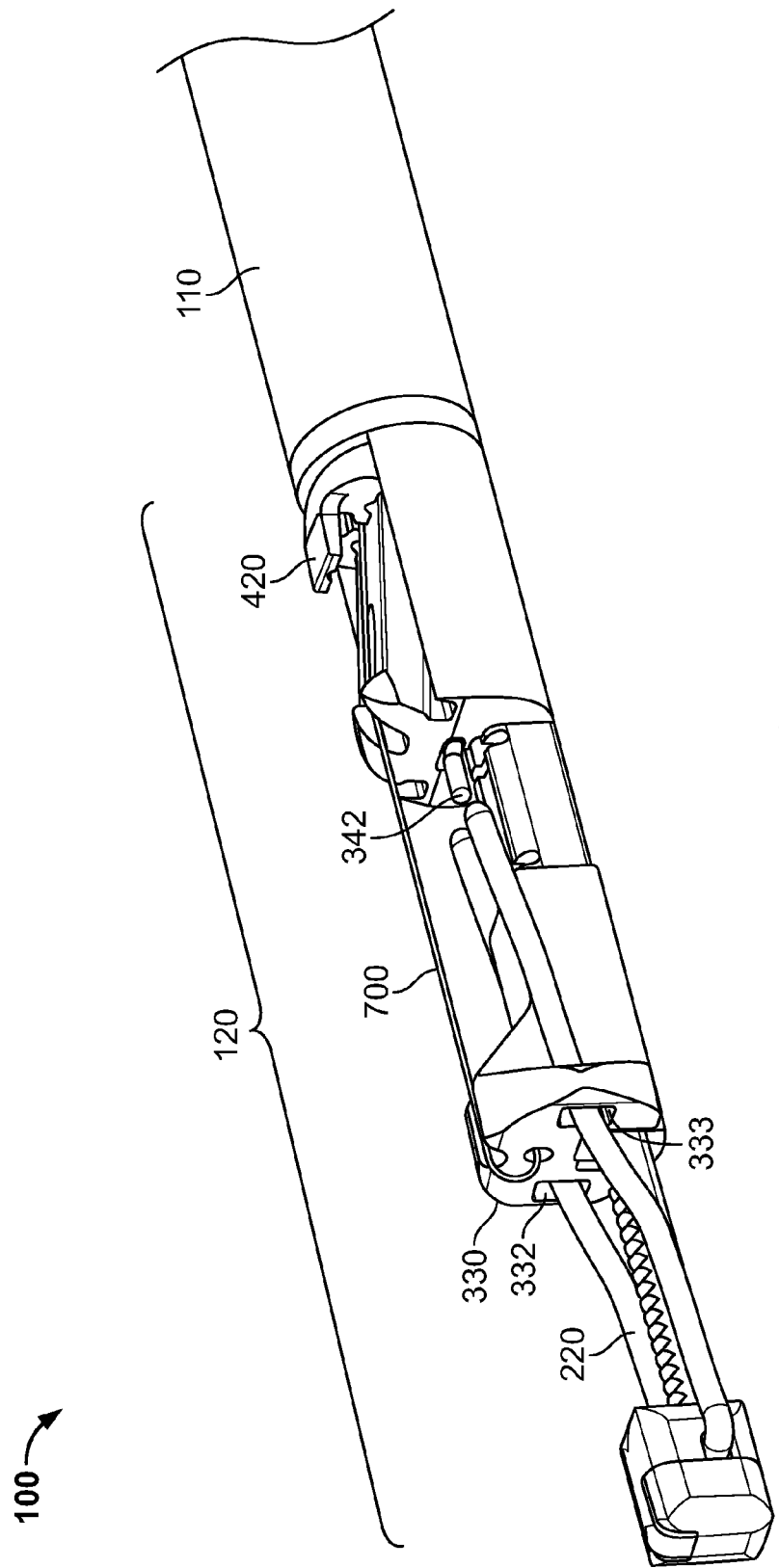
FIG. 9A is a perspective view of the repair device of FIG. 2 in a closed configuration.
Figure 9B:
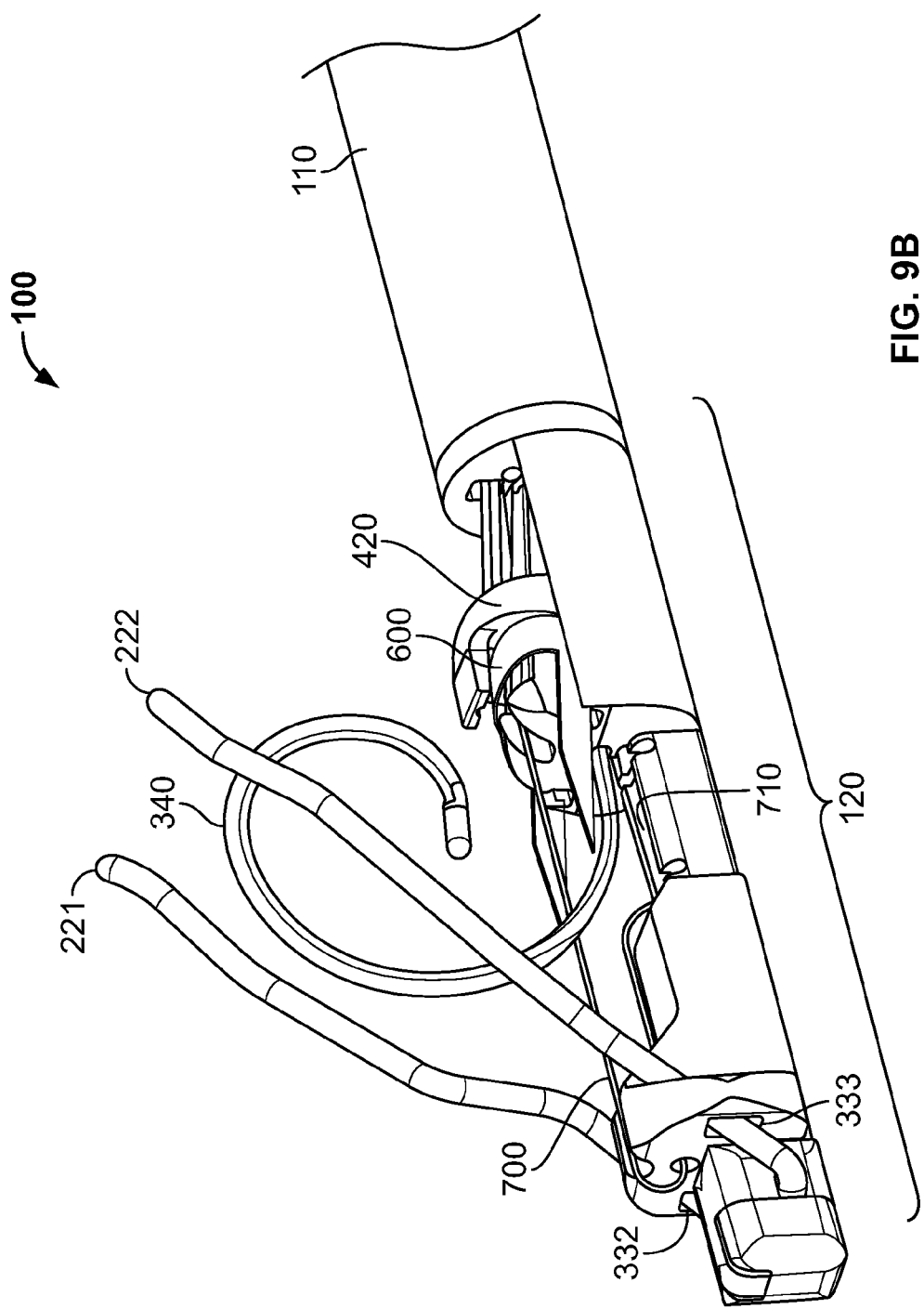
FIG. 9B is a perspective view of the repair device of FIG. 2 in an open configuration.

The distal face of the actuator 330 may also include an aperture 334 therethrough for accepting a portion of a safety tether 700 (illustrated in FIGS. 9A-B). The safety tether 700 may extend out of the aperture 334 and loop back across a groove 335 on the actuator 330 opposite the recess 331. The function of the safety tether 700 is described more fully below with reference to FIGS. 9A-D.

The clip housing 350 may be generally tubular or partially tubular-shaped with a recess 351 formed along the length of the clip housing 350. Similar to the recess 331 of the actuator 330, the recess 351 of the clip housing 350 may extend from a proximal end to a distal end of the clip housing 350. The recess 351 may generally correspond to the shape of the actuator rail 310 such that the recess 351 fits over the side walls 311, 312 of the actuator rail 310. The clip housing 350 may also include an aperture 352 extending the length of the clip housing 350. The aperture 352 may be generally rectangular and shaped to receive a plication wire 340, described in more detail below. The clip housing 350 may also include a groove 353. Similar to the actuator 330, a portion of the safety tether 700 may extend through the groove 353 and be guided by the groove 353.

The clip housing 350 may also include a ramp 356 and two clip slots 354, 355, each defined by the ramp 356 and an outer wall of the clip housing 350. The ramp 356 may be angled with respect to a longitudinal axis of the catheter assembly 110, for example with a distal end of the ramp protruding farther away from the longitudinal axis compared to a proximal end of the ramp. For example, the angle of the ramp 356 may be between about 5 and 15 degrees from a longitudinal axis of the repair device 100. As illustrated, the ramp 356 is angled at about 12 degrees. The clip slots 354, 355 each hold a portion of a clip 600 (FIGS. 8A-F) prior to delivering the clip 600 into tissue of the mitral valve 1. The ramp 356 of the clip housing 350 allows the clip 600 to be delivered at an angle into the tissue of the mitral valve 1 for improved contact between the clip 600 and the mitral valve 1.

The plication wire 340 extends from a proximal end (not shown) to an atraumatic tip 342, which may for example have a tear-drop shape, at a distal end of the plication wire 340. The plication wire 340 may extend proximally through a lumen 141 in the catheter assembly (FIG. 6A) and be operatively attached to the handle 500 to allow a user to advance or retract the plication wire 340. The plication wire 340 may be formed of a shape memory alloy, such as Nitinol. The plication wire 340 may be set with the shape of a loop or planar helix or spiral at the distal end when in an unconstrained configuration, as illustrated in FIG. 4. The plication wire 340 may be formed with a flat or rectangular cross section over the distal length 343 of the plication wire, corresponding to the aperture 352 in the clip housing 350. This flat section 343 may be shape-set into a planar helix whereby the radius of the bend decreases as the plication wire 340 loops to the center of the spiral at the tip 342. As is discussed below with reference to FIGS. 9A-D, when the tip 342 of the plication wire 340 resides in the aperture 352 of the clip housing 350, the plication wire 340 remains generally straight because it is constrained within the aperture 352. As the plication wire 340 is advanced distally out of the aperture 352, the plication wire 340 begins to revert to the set-shape, forming a loop or helix due to the shape memory properties of the plication wire 340. When reverting to the loop or helix shape, the distal section 343 of the plication wire 340 presses against the tissue of the mitral valve 1 to create a fold in the tissue. As is described in greater detail below with reference to FIGS. 9A-D, the plication wire 340 extends between the free ends 221, 222 of the capture wire 220, helping to create the fold in the tissue of the mitral valve 1. As the plication wire 340 is advanced even more distally, the loop or helix gets bigger in infinitesimally small increments to allow an infinite range of fold sizes up to the maximum diameter of the loop.

FIG. 5 illustrates the carriage assembly 400. The carriage assembly 400 generally includes an elongated carriage wire 410 that extends proximally through a lumen 141 of the catheter assembly 110 (FIG. 6A) and ultimately is operatively connected to the handle 500. The distal end of the carriage assembly 400 includes a carriage 420. The carriage 420 is shaped with two lateral extensions 421, 422 and a distal extension 423. The lateral extensions 421, 422 are shaped to fit into the clip slots 354, 355 of the clip housing 350 (FIG. 4). The distal extension 423 is shaped to contact a base portion 610 of the clip 600 (FIGS. 8A-F) as the clip 600 resides in the clip housing 350. As is described in more detail below with reference to FIG. 7, the handle 500 may be activated to advance the carriage wire 410, and thus the carriage 420, distally. This movement, in turn, advances the clip 600 from the clip housing 350, up the ramp 356, into the tissue of the mitral valve 1.

Now referring to FIGS. 6A-B, a portion of the catheter assembly 110 is illustrated. The catheter assembly may include an inner most core 140 with a plurality of lumens 141 defined therethrough. The lumens 141 may extend from the distal end of the catheter assembly 110 to the proximal end 130 (not illustrated in FIG. 6A) of the catheter assembly 110. The lumens 141 may serve, for example, to house wires connecting components of the distal tip 120 of the repair device 100 to the handle 500. The core 140 may be surrounded by a flexible tube 150, which may be formed of a biocompatible material, such as stainless steel. The flexible tube 150 may include a pattern 151 to increase the flexibility of the flexible tube 150. One exemplary pattern 151 is illustrated in greater detail in FIG. 6B. This pattern 151 generally includes parallel cut-out sections forming "H" shapes in the flexible tube 150. The flexible tube 150 may be surrounded by a jacket 160, which may be formed from a thermoplastic elastomer, such as polyether block amide, also known under the trade name PEBAX™. The jacket 160 may include patterning similar or identical to the pattern 151 of the flexible tube 150. FIGS. 6C-D show an alternate catheter assembly 110'. The catheter assembly 110' may be identical to the catheter assembly 110 in most respects. For example, it has an inner core 140' with a plurality of lumens 141', is surrounded by a flexible tube 150' that may be formed from stainless steel, and may include a jacket 160', which may be a thermoplastic elastomer such as polyether block amide or PEBAX™. However, the flexible tube 150' may have a different pattern 151', such as the helical pattern 151' illustrated in FIG. 6C and more particularly in FIG. 6D. Again, the jacket 160' may include patterning similar or identical to the helical pattern 151' of the flexible tube 150.

Figure 7:
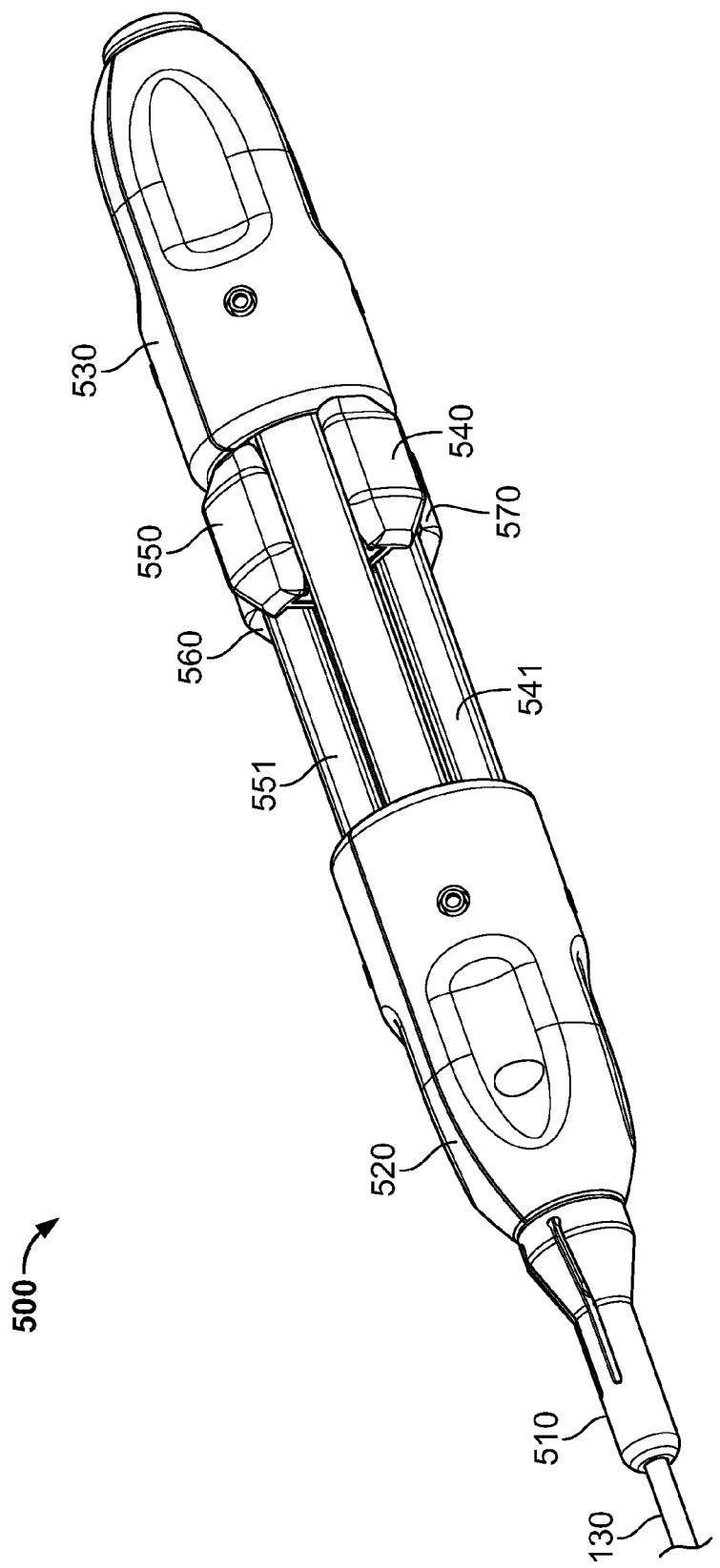
FIG. 7 is a perspective view of a handle for use with the repair device of FIG. 2.

FIG. 7 illustrates an exemplary handle 500 that may be used to control the catheter assembly 110 and components of the tip 120 of the repair device 100. The proximal end 130 of the catheter assembly 110, including wires extending through the catheter assembly 110, connect to and pass through a nose cone 510 of the handle 500. The handle 500 may include first and second grips 520, 530. A user may hold one or both of the grips 520, 530 while maneuvering the repair device 100.

Wires extending from the tip 120 of the repair device 100 to the handle 500 may be operatively connected to respective button assemblies for control of the wires. For example, the carriage wire 410 may extend through the catheter assembly 110 and be operatively connected to a clip button 540. The clip button 540 may be configured to slide along a button rail 541 between the first grip 520 and the second grip 530. A user may deliver a clip 600 (FIGS. 8A-F) by advancing the clip button 540 distally along the clip button rail 541. This, in turn, advances the carriage wire 410, and the attached carriage 420, which may be in contact with the clip 600. The handle 500 may also include a plication wire button 550, operatively attached to the proximal end of the plication wire 340. A user may slide the plication wire button 550 along a plication wire button rail 551 to advance or retract the plication wire 340. Similarly, the handle 500 may include an actuator button 560 operatively attached to the pivot tip wire 250. As a user slides the actuator button 560 along an actuator button rail (not visible in FIG. 7), the reinforcement tube 240 of the capture subassembly 200 (FIGS. 3A-B) is pulled proximally into the slot 314 of the actuator rail 310 (FIG. 4). As explained in more detail below with reference to FIGS. 9A-D, this movement causes the free ends 221, 222 of the capture wire 220 to pivot open or closed due to the interaction with the actuator 330. The handle 500 may further include a locking wire button 570 operatively attached to the locking wire 710. The locking wire button 570 may have three discrete positions. As a user slides the locking wire button from a middle position to a distal position, the locking wire 710 fills the vacant area between the locking element 322 and the top of the recess 331; thus prohibiting the capture wire 220 from moving. When the locking wire button 570 is moved proximally to the middle position, the actuator button 560 is free to move and control the position of the capture wire 220. When the locking wire button 570 is moved proximally to the full proximal position, the distal end of the locking wire 710 passes proximally through a loop in the safety tether 700, releasing the safety tether. The function and configuration of the safety tether 700 is described in greater detail below with reference to FIGS. 9A-D.

Figure 8A:
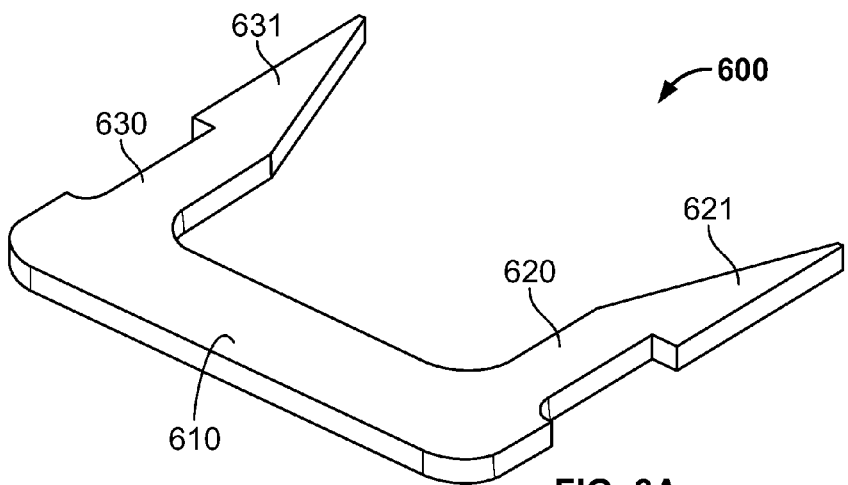
FIG. 8A is a perspective view of an unformed clip.
Figure 8B:
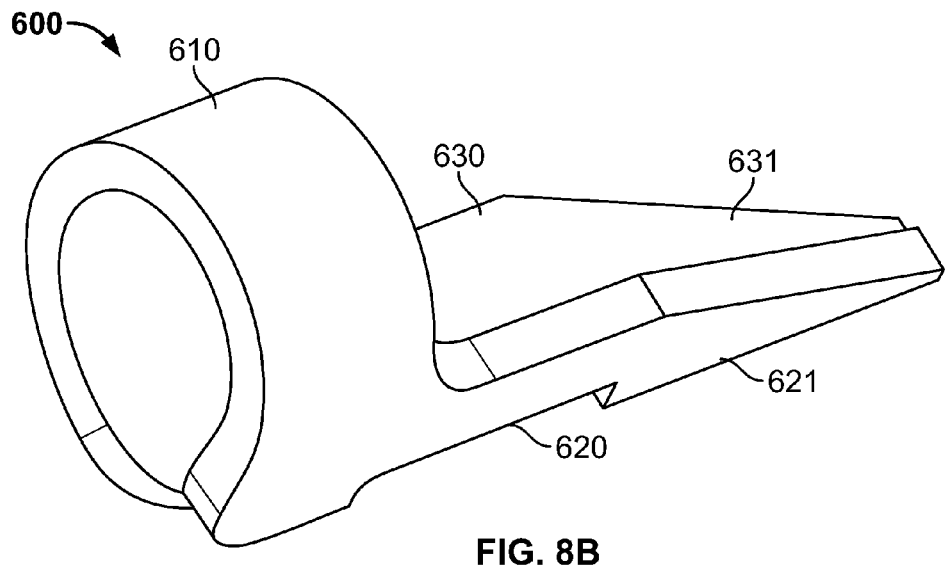
FIG. 8B is a perspective view of the clip of FIG. 8A after being shape-set.
Figure 8C:
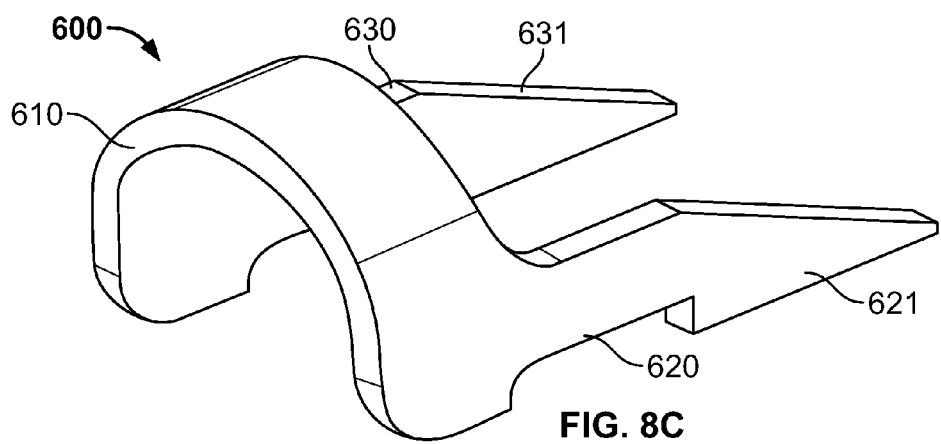
FIG. 8C is a perspective view of the clip of FIG. 8B when loaded on the repair device of FIG. 2.

FIGS. 8A-C illustrate a first example of a clip 600 that can be used in conjunction with the repair device 100. The clip 600 may be formed of a shape memory alloy, such as a nickel titanium alloy sold under the designation Nitinol. The clip 600 is illustrated in FIG. 8A in an unformed state, prior to having a particular shape set. The clip 600 generally includes a base 610 with two free ends 620, 630 extending generally perpendicular from the base 610. Each free end 620, 630 may include a barb 621, 631 at a distal end of the respective free end. The barbs 621, 631 assist the clip 600 in piercing the tissue of the mitral valve tissue 1, as is described in further detail below with reference to FIGS. 9A-D. The clip 600 may be shape-set, as illustrated in FIG. 8B. In the illustrated set shape, the base 610 is rounded with the free ends 620, 630 generally parallel and touching or nearly touching. Without external applied forces, the clip 600 tends to revert to the set shape when deployed as illustrated in FIG. 8B. This may be referred to as the deployed configuration. FIG. 8C illustrates the shape of the clip 600 once the clip 600 is loaded on the clip housing 350 of the ramp subassembly 300 (FIG. 4). This may be referred to as the loaded configuration. When loaded, the rounded base 610 is in contact with the ramp 356. The free ends 620, 630 of the clip 600 reside in the clip slots 354, 355 of the clip housing 350. Because of the contact between the rounded base 610 and the ramp 356, as well as the free ends 620, 630 of the clip 600 being situated in the clip slots 354, 355, the clip 600 is unable to revert to its set shape illustrated in FIG. 8B. Thus, while loaded, the clip 600 is in tension and reverts to the set shape once deployed from the repair device 100. As the clip 600 is deployed and reverts from the loaded configuration to the deployed configuration, the free ends 620, 630 of the clip may move toward each other. The clip 600 may also include an attachment feature (not illustrated) for a safety tether 700. For example, the base 610 may include a through-hole extending from a proximal end to a distal end of the base 610 through which a safety tether 700 may be threaded. This may ensure that an incorrectly or unintentionally deployed clip 600 may be retrieved while the safety tether 700 is still attached, as described in greater detail with reference to FIGS. 9A-D.

Figure 8D:
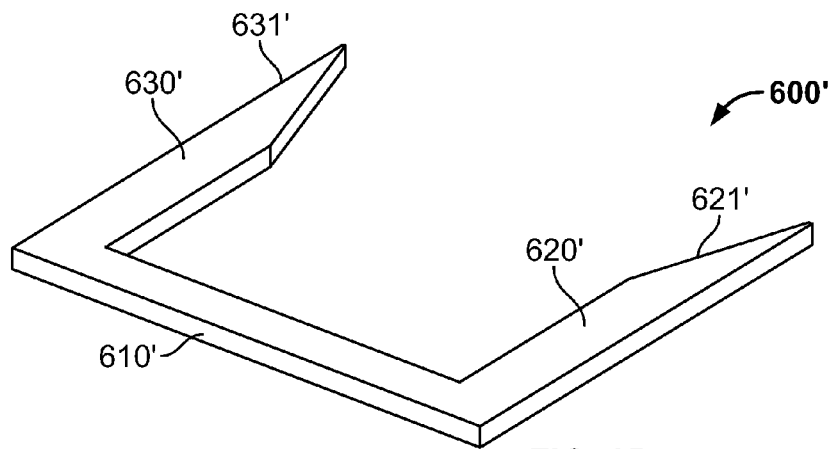
FIG. 8D is a perspective view of an alternate embodiment of an unformed clip.
Figure 8E:
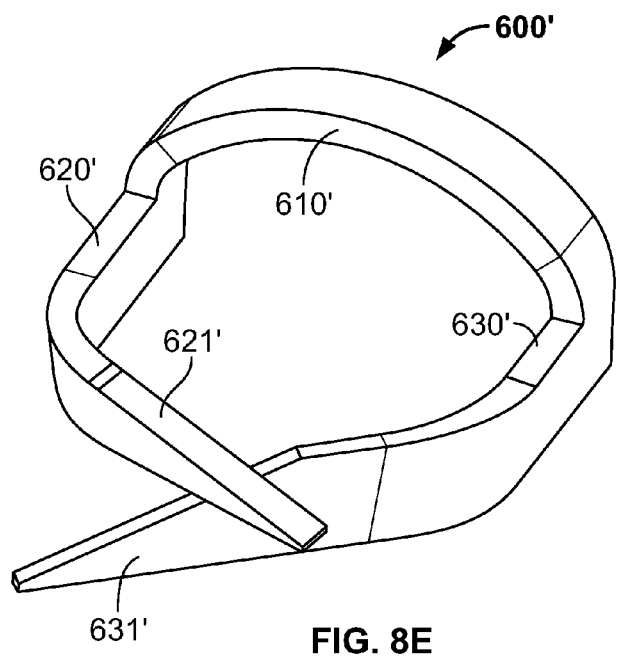
FIG. 8E is a perspective view of the clip of FIG. 8D after being shape-set.
Figure 8F:
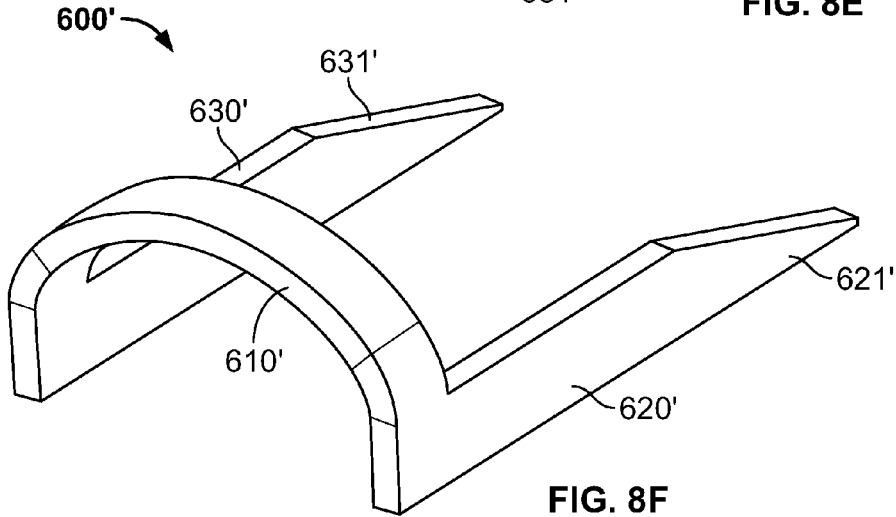
FIG. 8F is a perspective view of the clip of FIG. 8E when loaded on the repair device of FIG. 2.

FIGS. 8D-F illustrate a second example of a clip 600' that can be used in conjunction with the repair device 100. Again, the clip 600' may be formed of a shape memory alloy. The clip 600' is illustrated in FIG. 8D in an unformed state, prior to having a particular shape set. The clip 600' generally includes a base 610' with two free ends 620', 630' extending generally perpendicular from the base 610'. The distal end of each free end 620', 630' may include a sharp tip 621', 631'. The sharp tips 621', 631' assist the clip 600' in piercing the tissue of the mitral valve tissue 1, as is described in further detail below. The clip 600' may be shape-set as illustrated in FIG. 8E. In the illustrated set shape, also referred to as the deployed configuration, the base 610' is rounded with the sharp tips 621', 631' of free ends 620', 630' crossing over towards each other. Without external applied forces, the clip 600' tends to revert to the set shape illustrated in FIG. 8E. FIG. 8F illustrates the shape of the clip 600' once the clip 600' is loaded on the clip housing 350 of the ramp subassembly 300 (FIG. 4). This may be referred to as the loaded configuration. The loading may be identical to that described with reference to the clip 600. Again, while loaded, the clip 600' is in tension and, as is described below, reverts to the set shape once deployed from the repair device 100. As the clip 600' is deployed and transforms from the loaded configuration to the deployed configuration, the free ends 620', 630' change from being generally parallel to being antiparallel with respect to each other. The clip 600' may also include an attachment feature (not illustrated) for the safety tether 700.

FIGS. 9A-B show the repair device 100 in a closed delivery configuration and an open configuration, respectively. The operation of the repair device 100 is described with reference to FIGS. 9A-D, although reference may be made to features described in previous FIGS. Generally, the repair device 100 is used to capture, fold, and deliver the clip 600 to a mitral valve leaflet 2 to reduce the effects of mitral regurgitation. The repair device 100 may be used with a separate guide catheter device (not illustrated) that provides access to the left atrium via femoral access and steering the repair device 100 to the target therapy site. Once the guide catheter has provided access to the left atrium, the repair device 100 is passed through until the distal tip 120 exits the guide catheter. As the repair device 100 is advanced through the guide catheter, it is in the closed configuration illustrated in FIG. 9A, with the capture wire 220 generally parallel to the longitudinal axis of the catheter assembly 110. Similarly, in the closed configuration, the distal section 343 of the plication wire 340 is mostly within the aperture 352 of the clip housing 350. In FIG. 9A, only the distal tip 342 of the plication wire 340 is shown as protruding beyond the aperture 352 of the clip housing 350.

Once the distal tip 120 of the repair device 100 exits the distal end of the guide catheter, the guide catheter and the repair device 100 work in concert. Advancement, retraction, and rotation of the distal tip 120 are controlled with the repair device 100, while multi-directional steering is provided by the guide catheter as is known in the art. The distal tip 120 of the delivery device is advanced through the mitral valve 1 into the left ventricle and positioned below the target leaflet 2. The repair device 100 is rotated to position the free ends 221, 222 of the capture wire 220 towards the target leaflet 2. Once in the desired position, the user retracts the actuator button 560, moving reinforcing tube 240 of the capture subassembly 200 proximally. As the capture subassembly 200 moves proximally, the actuator 330 remains fixed in position, the free ends 221, 222 of the capture wire 220 moving proximally further through the through-holes 332, 333 of the actuator 330. As the free ends 221, 222 of the capture wire 220 move proximally across the ramped surface of the through-holes 332, 333, the central portion 223 of the capture wire 220 rotates while secured between the pivot tip 230 and pivot tip lock 210. The free ends 221, 222 of the capture wire 220 simultaneously rotate towards the open position, as seen in FIG. 9B. As described above, the textured surface 241 of the reinforcing tube 240 may interact with the locking element 322 of the actuator lock 320. This may allow the user to rotate the capture wire 220 from the closed position to the open position (or vice versa) in discrete increments, while simultaneously inhibiting accidental rotation of the capture wire 220 without intentional force being applied to the actuator button 560. If positioned correctly, the leaflet 2 of the mitral valve 1 is positioned between the free ends 221, 222 of the capture wire and the distal tip 120 of the repair device 100. Fluoroscopy and/or echocardiography may be utilized by the user to determine proper positioning of the device.

The distal tip 120 of the device is then positioned such that the free ends 221, 222 of the capture wire 220 are on the inferior side of the leaflet 2 and the catheter assembly 110 is exposed to the superior side of the leaflet 2. Once proper placement is confirmed through visualization, the capture wire 220 is rotated back to the closed position by sliding the actuator button 560 in the opposite direction. This action causes the free ends 221, 222 of the capture wire 220 to pivot or rotate back toward the tip 120, trapping the leaflet tissue between the capture wire 220 and the tip 120, as illustrated in FIG. 9C.

At this point the leaflet 2 of the mitral valve 1 is captured and its systolic motion retarded. If the capture is determined not optimal, the capture wire 220 may be opened again using the actuator button 560, releasing the leaflet 2, and allowing the user to reposition the capture wire 220, and recapture the leaflet 2 in the desired location.

Figure 9C:
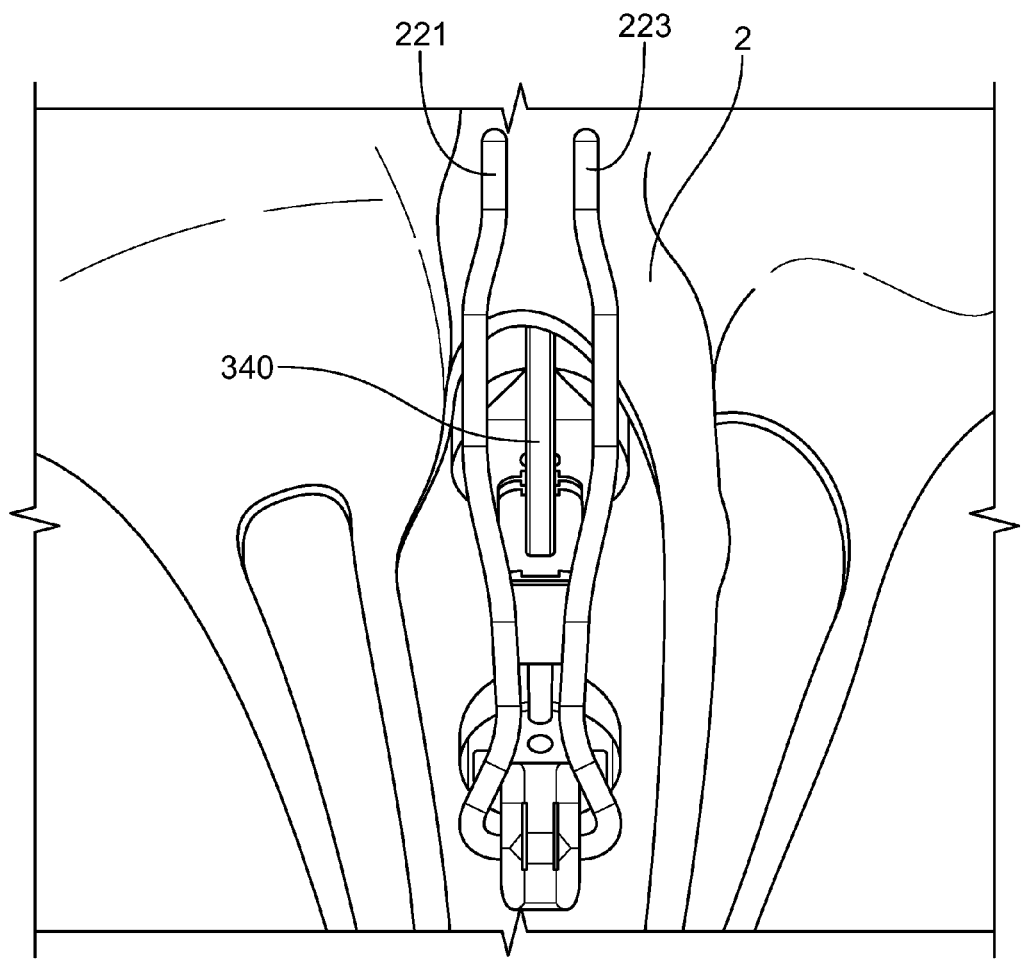
FIG. 9C shows a repair device positioned on a leaflet of a mitral valve.
Figure 9D:
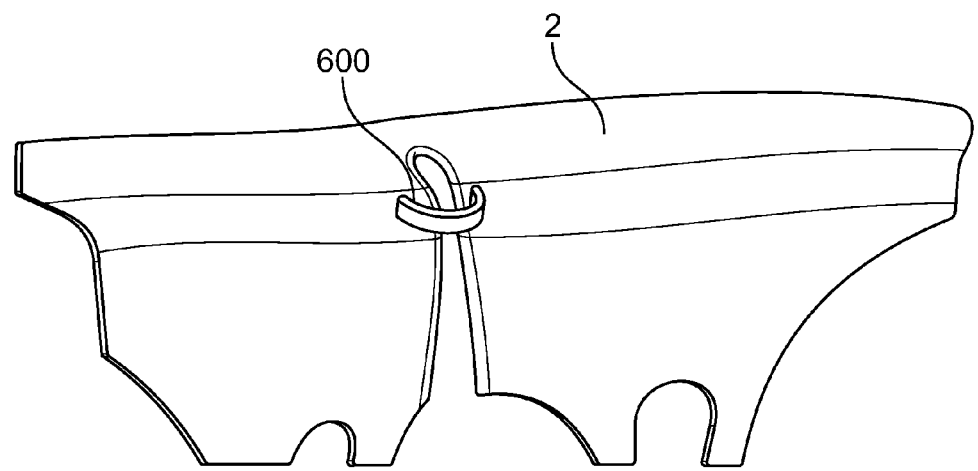
FIG. 9D shows the leaflet of the mitral valve after a clip has been deployed into the leaflet.

Once the leaflet 2 is captured, the user then advances the plication wire 340 into the open position by advancing the plication wire button 550 on the handle 500, as illustrated in FIGS. 9B-C. Note that in FIG. 9B, the free ends 221, 222 of the capture wire 220 and the plication wire 340 are shown as simultaneously being in the open position. This would not necessarily occur, as the plication wire 340 is advanced into the open position once the capture wire 220 is in the closed position and the leaflet 2 is captured therein. However, both the capture wire 220 and plication wire 340 are shown in the open configuration simultaneously to illustrate the relative positioning of the plication wire 340 between the free ends 221, 222 of the capture wire 220. As the plication wire 340 is advanced farther distally and it begins to revert to its set-shape, the diameter of the loop continues to increase up to a maximum. As the diameter increases, the plication wire 340 pushes increasingly on captured tissue. In this way the operator can expose an ever increasing amount of the plication wire 340 and thereby create a larger fold/plication in the tissue. This process is variable, not discrete, to allow for the widest range of possible fold sizes and therefore the widest range of therapy conditions. By creating this fold the excess tissue causing the mitral regurgitation is displaced and the desired amount of tension/tightening of the leaflet 2 achieved.

Once the desired amount of plication has been created and verified under visualization, the operator may reposition the plication wire 340 or choose to deploy the clip 600 to secure the fold. As noted above, the repair device 100 may include a safety tether 700. Generally, the safety tether 700 is a suture (or other suitable material) that passes through an eyelet (not shown) of the clip 600. One end of the safety tether 700 may be permanently attached to the distal end of the catheter assembly 110. The other end of the safety tether 700 may have a closed loop formed at the tip. The safety tether 700 may extend through the grooves 335, 353 in the actuator 330 and clip housing 350. As illustrated in FIGS. 9A-B, the safety tether 700 is positioned parallel to the actuator rail 310, outside of the distal components of the tip 120, and enters into the proximal base of the actuator 330. The safety tether 700 may loop back proximally, the end of the safety tether forming a closed loop through which locking wire 710 extends. In this configuration, the safety tether 700 is enclosed over the length of the catheter assembly 110 and at the tip 120 within the actuator 330, with only the exposed length described above outside of the catheter 110. With this configuration, the looped end of the safety tether 700 is captured in the space between the actuator 330 and clip housing 350, just above the actuator rail 310. The length of the safety tether 700 also passes through an eyelet of the clip 600, tethering the clip to the distal end of the catheter assembly 110. As described above in relation to FIG. 7, when the locking wire button 570 (and locking wire 710) is in the middle and distal positions, the locking wire extends through the looped end of the safety tether 700, securing both ends of the safety tether. When moved into the proximal position, the locking wire 710 moves proximally and clears the loop in the safety tether 700, freeing that end of the safety tether to pass through the eyelet of the clip 600 and thus release the clip.

To deploy the clip 600, the user advances the clip button 540 on the handle 500. Advancing the clip button 540 advances the carriage wire 410 and thus the carriage 420. The clip 600, being in contact with the carriage 420, is also advanced as the carriage 420 advances. As the clip 600 advances, it slides up the ramp 356 of the clip housing 350. The free ends 620, 630 of the clip 600 move distally and the barbs 621, 631 pierce the superior face of the folded leaflet 2. As discussed above, the clip 600 is housed in the clip housing 350 which is shaped to maintain the clip 600 in tension. As the clip 600 advances, the free ends 221, 222 of the capture wire 220 serve as anvils to aid the puncture. Once driven fully distally and released from the constraints of the clip housing 350, the clip 600 returns to its relaxed form, compressing the sides of the folded tissue together as a permanent implant. Since the clip 600 spans each side of the tissue fold, the fold is held securely in place. The clip 600 is illustrated in its final position in the leaflet 2 in FIG. 9D.

The plication wire 340 is then retracted by retracting the plication wire button 550 and the capture wire 220 is set to the open position by retracting the actuator button 560 to release the leaflet 2, returning to its normal systolic cycle. The effectiveness of the therapy can then be assessed using imaging, such as Doppler imaging on sonography equipment.

Given a successful deployment of the clip 600 the operator then releases the safety tether loop 700. As described above, this release is accomplished by retracting the locking wire button 570 proximally, retracting the locking wire 710 attached to the button into the clip housing 350. With the locking wire 710 retracted within the clip housing 350, the looped end of the safety tether 700 is freed from the locking wire 710, allowing it to pass through the eyelet of the clip 600, releasing the clip from the device. Should the clip 600 be unsuccessfully deployed, the safety tether 700 prevents downstream migration. The repair device 100 is then retracted into the guide catheter and the system removed from the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

Certain aspects of the disclosure are summarized in the paragraphs below.

Paragraph A: A device for repair of a heart valve leaflet comprises an elongated catheter assembly having (i) a proximal end and a distal end, (ii) a tip at the distal end of the catheter assembly, (iii) a capture mechanism having a first free end and a second free end and being rotatably coupled to a distal end of the tip, (iv) a plication mechanism having an open configuration and a closed configuration, the plication mechanism extending between the first free end and the second free end of the capture mechanism when in the open configuration, and (v) a clip housing at a proximal end of the tip configured to hold a clip therein.

Paragraph B: The device of Paragraph A, wherein the plication mechanism is a wire.

Paragraph C: The device of any of the above Paragraphs, wherein the plication wire is formed from shape-memory alloy.

Paragraph D: The device of any of the above Paragraphs, wherein the plication wire includes an atraumatic tip at a distal end thereof.

Paragraph E: The device of any of the above Paragraphs, wherein a distal section of the plication wire has a generally rectangular cross section.

Paragraph F: The device of any of the above Paragraphs, wherein the distal section of the plication wire has the shape of a spiral when in the open configuration.

Paragraph G: The device of any of the above Paragraphs, wherein the distal section of the plication wire is generally parallel to a longitudinal axis of the catheter assembly when in the closed configuration.

Paragraph H: The device of any of the above Paragraphs, wherein the plication wire is advanceable from the closed configuration to the open configuration, and wherein a diameter of the spiral increases in infinitesimally small increments up to a maximum diameter as the plication wire is advanced from the closed configuration to the open configuration.

Paragraph I: The device of any of the above Paragraphs, wherein the capture mechanism is a wire.

Paragraph J: The device of any of the above Paragraphs, wherein the capture wire is generally "U"-shaped or generally "V"-shaped.

Paragraph K: The device of any of the above Paragraphs, further comprising an actuator having a first through-hole and a second through-hole, wherein the first free end of the capture mechanism is at least partially housed in the first through-hole and the second free end of the capture mechanism is at least partially housed in the second through-hole.

Paragraph L: The device of any of the above Paragraphs, further comprising a clip in the clip housing.

Paragraph M: The device of any of the above Paragraphs, wherein the clip has a base and two free ends extending from the base.

Paragraph N: The device of any of the above Paragraphs, wherein the two free ends are barbed.

Paragraph O: The device of any of the above Paragraphs, wherein the clip is formed of a shape-memory alloy and has a loaded configuration and a deployed configuration.

Paragraph P: The device of any of the above Paragraphs, wherein the clip tends to revert from the loaded configuration to the deployed configuration when no external forces are applied to the clip.

Paragraph Q: The device of any of the above Paragraphs, wherein the base of the clip is rounded, and further wherein the two free ends of the clip are spaced farther apart when in the loaded configuration compared to the deployed configuration.

Paragraph R: The device of any of the above Paragraphs, wherein the base of the clip is rounded, and further wherein the two free ends of the clip are generally parallel in the loaded condition and are anti-parallel when in the deployed configuration.

Paragraph S: The device of any of the above Paragraphs, wherein the clip housing has a ramped portion that is angled with respect to a longitudinal axis of the catheter assembly.

Paragraph T: The device of any of the above Paragraphs, wherein the ramped portion has an angle of between about 10 degrees and about 15 degrees with respect to the longitudinal axis of the catheter assembly.

Paragraph U: A device for repair of a heart valve leaflet comprising (i) an elongated catheter assembly having a proximal end and a distal end, (ii) a tip at the distal end of the catheter assembly, (iii) a generally "V"-shaped capture wire having a first free end and a second free end and being rotatably coupled to a distal end of the tip, (iv) a plication wire formed from a shape-memory alloy having an open configuration and a closed configuration, the plication mechanism extending between the first free end and the second free end of the capture mechanism when in the open configuration, the plication wire including an atraumatic tip at a distal end thereof, (v) a clip housing at a proximal end of the tip configured to hold a clip therein, the clip housing having a ramped portion that is angled with respect to a longitudinal axis of the catheter assembly, (vi) an actuator having a first through-hole and a second through-hole, wherein the first free end of the capture wire is at least partially housed in the first through-hole and the second free end of the capture wire is at least partially housed in the second through-hole, and (vii) a clip formed from a shape-memory alloy in the clip housing, the clip having a base and two free ends extending from the base and also having a loaded configuration and a deployed configuration, wherein the clip tends to revert from the loaded configuration to the deployed configuration when no external forces are applied to the clip.

Paragraph V: A device for repair of a heart valve leaflet comprises an elongated catheter assembly having (i) a proximal end and a distal end, (ii) a tip at the distal end of the catheter assembly, (iii) a capture mechanism coupled to a distal end of the tip, (iv) a plication mechanism, (v) a clip housing at a proximal end of the tip configured to hold a clip therein, and (vi) a clip formed of a shape-memory alloy in the clip housing, the clip having a base and two free ends extending from the base and having a loaded configuration and a deployed configuration, wherein the clip tends to revert from the loaded configuration to the deployed configuration when no external forces are applied to the clip.

Paragraph W: A device for repair of a heart valve leaflet comprises an elongated catheter assembly having (i) a proximal end and a distal end, (ii) a tip at the distal end of the catheter assembly, (iii) a capture mechanism coupled to a distal end of the tip, (iv) a plication wire formed from a shape-memory alloy having an open configuration and a closed configuration and having an atraumatic tear-drop shaped tip at a distal end thereof, and (v) a clip housing at a proximal end of the tip configured to hold a clip therein.

Paragraph X: A device for repair of a heart valve leaflet comprises an elongated catheter assembly having (i) a proximal end and a distal end, (ii) a tip at the distal end of the catheter assembly, (iii) a capture mechanism coupled to a distal end of the tip, (iv) a plication wire formed from a shape-memory alloy having an open configuration and a closed configuration, wherein a distal section of the plication wire has a generally rectangular cross section and has the shape of a spiral when in the open configuration and (v) a clip housing at a proximal end of the tip configured to hold a clip therein.

Paragraph Y: A device for repair of a heart valve leaflet comprises an elongated catheter assembly having (i) a proximal end and a distal end, (ii) a tip at the distal end of the catheter assembly, (iii) a capture mechanism coupled to a distal end of the tip, (iv) a plication mechanism having an open configuration and a closed configuration, and (v) a clip housing at a proximal end of the tip configured to hold a clip therein, the clip housing having a ramped portion that is angled with respect to a longitudinal axis of the catheter assembly, wherein the plication mechanism is configured to be in the closed configuration when a distal end thereof is positioned within the clip housing and the plication mechanism is configured to advance to the open configuration as the distal end of the plication mechanism advances out of the clip housing.

Paragraph Z: A device for repair of a heart valve leaflet comprises an elongated catheter assembly having (i) a proximal end and a distal end, (ii) a tip at the distal end of the catheter assembly, (iii) a capture mechanism having a first free end and a second free end and being rotatably coupled to a distal end of the tip, (iv) a plication wire having an open configuration and a closed configuration, the plication mechanism extending between the first free end and the second free end of the capture mechanism when in the open configuration, and (v) a clip housing at a proximal end of the tip configured to hold a clip therein, (vi) wherein a distal section of the plication wire has the shape of a spiral when in the open configuration and is generally parallel to a longitudinal axis of the catheter assembly when in the closed configuration, the plication wire being advanceable from the closed configuration to the open configuration, and wherein a diameter of the spiral increases in infinitesimally small increments up to a maximum diameter as the plication wire is advanced from the closed configuration to the open configuration.

Paragraph AA: A device for repair of a heart valve leaflet comprises an elongated catheter assembly having (i) a proximal end and a distal end, (ii) a tip at the distal end of the catheter assembly, (iii) a capture mechanism coupled to a distal end of the tip, (iv) a plication mechanism, (v) a clip housing at a proximal end of the tip configured to hold a clip therein, and (vi) a clip formed of a shape-memory alloy in the clip housing, the clip having a base and two free ends extending from the base and having a loaded configuration when the clip is within the clip housing and a deployed configuration, wherein the clip housing applies force to the clip when the clip is within the clip housing to maintain the clip in the loaded configuration.

Paragraph BB: A device for repair of a heart valve leaflet comprises an elongated catheter assembly having (i) a proximal end and a distal end, (ii) a tip at the distal end of the catheter assembly, (iii) a capture mechanism coupled to a distal end of the tip, (iv) a plication mechanism, (v) a clip housing at a proximal end of the tip configured to hold a clip therein, (vi) a clip formed of a shape-memory alloy in the clip housing, and (vii) a safety tether coupled to both the clip and the catheter assembly.

Paragraph CC: The device of any of Paragraphs A-T, further comprising a safety tether coupled to both the clip and the catheter assembly.

The invention claimed is:

1. A device for repair of a heart valve leaflet comprising:
an elongated catheter assembly having
a proximal end and a distal end;
a tip at the distal end of the catheter assembly;
a capture mechanism having a first free end and a second free end and being rotatably coupled to a distal end of the tip so that the first and second free ends extend toward the proximal end of the catheter assembly;
a plication mechanism having an open configuration and a closed configuration, the plication mechanism extending between the first free end and the second free end of the capture mechanism when the capture mechanism is in a closed configuration and the plication mechanism is in the open configuration;
a clip housing at a proximal end of the tip configured to hold a clip therein; and
an actuator having a first through-hole and a second through-hole, wherein the first free end of the capture mechanism is at least partially housed in the first through-hole and the second free end of the capture mechanism is at least partially housed in the second through hole, the through-holes providing a ramped surface, where movement of the actuator with respect to the first and second free ends of the capture mechanism causes rotation of the capture mechanism between an open configuration and the closed configuration configured to capture the leaflet, the plication mechanism operable to fold the captured leaflet, and the clip housing oriented and configured to deploy the clip onto the folded captured leaflet.

2. The device of claim 1, wherein the plication mechanism is a wire.

3. The device of claim 2, wherein the plication wire is formed from shape-memory alloy.

4. The device of claim 3, wherein the plication wire includes an atraumatic tip at a distal end thereof.

5. The device of claim 2, wherein a distal section of the plication wire has a generally rectangular cross section.

6. The device of claim 5, wherein the distal section of the plication wire has the shape of a spiral when in the open configuration.

7. The device of claim 6, wherein the distal section of the plication wire is generally parallel to a longitudinal axis of the catheter assembly when in the closed configuration.

8. The device of claim 7, wherein the plication wire is advanceable from the closed configuration to the open configuration, and wherein a diameter of the spiral increases in infinitesimally small increments up to a maximum diameter as the plication wire is advanced from the closed configuration to the open configuration.

9. The device of claim 1, wherein the capture mechanism is a wire.

10. The device of claim 9, wherein the capture wire is generally "U"-shaped or generally "V"-shaped.

11. The device of claim 1, further comprising a clip in the clip housing.

12. The device of claim 11, wherein the clip has a base and two free ends extending from the base.

13. The device of claim 12, wherein the two free ends are barbed.

14. The device of claim 11, wherein the clip is formed of a shape-memory alloy and has a loaded configuration and a deployed configuration.

15. The device of claim 14, wherein the clip tends to revert from the loaded configuration to the deployed configuration when no external forces are applied to the clip.

16. The device of claim 15, wherein the base of the clip is rounded, and further wherein the two free ends of the clip are spaced farther apart when in the loaded configuration compared to the deployed configuration.

17. The device of claim 15, wherein the base of the clip is rounded, and further wherein the two free ends of the clip are generally parallel in the loaded condition and are anti-parallel when in the deployed configuration.

18. The device of claim 1, wherein the clip housing has a ramped portion that is angled with respect to a longitudinal axis of the catheter assembly.

19. The device of claim 1, further comprising a safety tether coupled to both the clip and the catheter assembly.

* * * * *